United States Patent
Blume et al.

[11] Patent Number: 6,157,853
[45] Date of Patent: Dec. 5, 2000

[54] METHOD AND APPARATUS USING SHAPED FIELD OF REPOSITIONABLE MAGNET TO GUIDE IMPLANT

[75] Inventors: Walter M. Blume, Webster Groves, Mo.; Rogers C. Ritter, Charlottesville, Va.; Peter R. Werp, Los Gatos, Calif.; Bevil J. Hogg, Town & Country, Mo.; Matthew A. Howard, III, Iowa City, Iowa

[73] Assignee: Stereotaxis, Inc., St. Louis, Mo.

[21] Appl. No.: 09/020,934

[22] Filed: Feb. 9, 1998

Related U.S. Application Data
[60] Provisional application No. 60/065,103, Nov. 12, 1997.

[51] Int. Cl.$^7$ .................................................. A61B 5/055
[52] U.S. Cl. ........................................... 600/426; 606/130
[58] Field of Search .................................. 600/407, 410, 600/426, 130; 378/20, 205; 324/309

[56] References Cited

U.S. PATENT DOCUMENTS

| | | | |
|---|---|---|---|
| 3,358,676 | 12/1967 | Frei et al. | 128/1.3 |
| 3,674,014 | 7/1972 | Tillander | 128/2.05 R |
| 4,364,377 | 12/1982 | Smith | 128/1.5 |
| 4,869,247 | 9/1989 | Howard, III et al. | 128/303.1 |
| 4,875,485 | 10/1989 | Matsutani | 128/653 |
| 4,923,459 | 5/1990 | Nambu | 606/130 |
| 5,125,888 | 6/1992 | Howard et al. | 600/12 |
| 5,153,546 | 10/1992 | Laskaris et al. | 335/216 |
| 5,230,338 | 7/1993 | Allen et al. | 128/653 |
| 5,304,930 | 4/1994 | Crowley et al. | 324/309 |
| 5,332,987 | 7/1994 | Hennessy et al. | 335/216 |
| 5,334,207 | 8/1994 | Gay, Jr. | 606/7 |
| 5,436,607 | 7/1995 | Chari et al. | 335/216 |
| 5,558,091 | 9/1996 | Acker et al. | 128/653.1 |
| 5,588,430 | 12/1996 | Bova et al. | 128/653.1 |
| 5,622,170 | 4/1997 | Schulz | 128/653.1 |
| 5,654,864 | 8/1997 | Ritter et al. | 361/141 |
| 5,681,260 | 10/1997 | Ueda et al. | 600/114 |
| 5,833,608 | 11/1998 | Acker | 600/409 |
| 5,845,646 | 12/1998 | Lemelson | 128/899 |
| 5,848,967 | 12/1998 | Cosman et al. | 600/426 |
| 5,853,367 | 12/1998 | Chalek et al. | 600/437 |
| 5,891,034 | 4/1999 | Bucholz | 600/426 |

FOREIGN PATENT DOCUMENTS

WO 96/03795  2/1996  WIPO ............................ H02N 15/00

OTHER PUBLICATIONS

"Characteristics of an Improved Magnetic–Implant Guidance System," Robert G. McNeil et al., IEEE Trans. Biomed. Eng., vol. 42, No. 8, Aug. 1995, pp. 802–808.

"Functional Design Features and Initial Performance Characteristics of a Magnetic–Implant Guidance System for Stereotactic Neurosurgery," Robert G. McNeil et al., IEEE Trans. Biomed. Eng., vol. 42, No. 8, Aug. 1995, pp. 793–801.

(List continued on next page.)

*Primary Examiner*—Marvin M. Lateef
*Assistant Examiner*—Eleni Mantis Mercader
*Attorney, Agent, or Firm*—Bryan K. Wheelock

[57] ABSTRACT

Methods and apparatuses for displaying and using a shaped field of a repositionable magnet to move, guide, and/or steer a magnetic seed or catheter in living tissue for medicinal purposes. A moveable magnet assembly and a portion of a patient's body undergoing magnetically-aided surgery are both provided with fiducial markers. The portion of the patient's body is fixed in a location in which the fiducial markers are sensed and located by a set of localizers. The positions of the fiducial markers are determined by a processor, which operates on a stored representation of the magnetic field of a magnet in the magnet assembly to provide a display of the present magnetic field of the magnet. This display may be superimposed over an MRI, X-ray or CAT image during surgery. The repositionable magnet can be an electromagnet. In some embodiments, a computer calculates orientations and currents for an external electromagnet to move the implanted magnetic object in the patient's body through a desired path. The display can provide real-time imaging of the implanted magnetic object in comparison to the desired path as the object is moved.

26 Claims, 4 Drawing Sheets

OTHER PUBLICATIONS

"Magnetic Manipulation Instrumentation for Medical Physics Research," G.T. Gillies et al., Rev. Sci. Instrum. 65 (3); Mar. 1994, pp. 533–562.

"Goniometric Motion Controller for the Superconducting Coil in a Magnetic Stereotaxis System," Elizabeth G. Quate et al., IEEE Trans. Biomed. Eng., vol. 38, No. 9, Sep. 1991, pp. 899–905.

"Nonlinear magnetic stereotaxis: Three–dimensional, in vivo remote magnetic manipulation of a small object in canine brain," M.S. Grady et al., Med. Phys. 17 (3), May/Jun. 1990, pp. 405–415.

"External Magnetic Guidance of Endovascular Catheters With a Superconducting Magnet: Preliminary Trials," A. Gaston et al., J. Neuroradiol 1988, 15, pp. 137–147.

"A review of medical application of magnet attractions and detection," Jack Driller et al., Journal of Med. Eng. & Tech., vol. 11, No. 6, Nov./Dec. 1987, pp. 271–277.

"Magnetically Guided Devices for Vascular Exploration and Treatment," Sadek K. Hilal, et al., Radiology 113, Dec. 1974, pp. 529–540.

"Kinetics of Magnetically Guided Catheters," Jack Driller, IEEE Transactions on Magnetics, vol. MAG–6, No. 3, Sep. 1970, pp. 467–471.

"Selective Angiography with a Catheter Guided by a Magnet," H. Tillander, IEEE Transactions on Magnetics, vol. MAG–6, No. 2, Jun. 1970, pp. 355–358.

"Selective Cerebral Catheterization," Jonathan Molcho et al., IEEE Trans. Bio. Med. Eng., vol. BME–17, No. 2, Apr. 1970, pp. 134–140.

"Superconducting Magnet System for Intravascular Navigation," D.B. Montgomery et al., Journal of Applied Physics, vol. 40, No. 5, Apr. 1969, pp. 2129–2132.

"Magnetism and Medicine," E.H. Frei, Journal of Applied Physics, vol. 40, No. 3, Mar. 1969, pp. 955–957.

"Symposium on Bioengineering: Magnetic Forces for Medical Applications," D.B. Montgomery et al., Journal of Applied Physics, vol. 40, No. 3, Mar. 1969, pp. 1039–1041.

"A New Magnet System For 'Intravascular Navigation'," Shyam B. Yodh et al., Med. And Bio. Eng., vol. 6, 1968, pp. 143–147.

METHOD AND APPARATUS USING SHAPED FIELD OF REPOSITIONABLE MAGNET TO GUIDE IMPLANT

CROSS-REFERENCE TO RELATED APPLICATION

This application claims the benefit of U.S. Provisional Application No. 60/065,103, filed Nov. 12, 1997, entitled "Method and Apparatus Using Shaped Field of Repositionable Magnet to Guide Implant," and which is herein incorporated by reference in its entirety.

BACKGROUND OF THE INVENTION

1. Field of the Invention

This invention relates to devices and methods for using a magnetic field to guide a surgical implant, and more specifically to devices and methods for using the near field and transition field of a repositionable magnet to move, guide, and/or steer a magnetic seed, catheter or other magnetic delivery vehicle (MDV) for therapeutic or surgical purposes.

2. Description of Related Art

In the field of surgery, there exists a need to control the orientation, forces, and/or motion of internally implanted devices. One method that has been used to control such implanted devices is the application of a magnetic field from an external magnet. In this method, the magnetic field acts upon the implanted device, which itself comprises magnetic material, which may be in the form of a permanent magnet. In accordance with prior art practice, a physician surgically implants the device comprising magnetic material and then guides the position of the implanted device by moving an external permanent magnet and observing the resultant movement directly with an X-ray fluoroscope. Examples of the prior art may be found in a review article by Gillies et al., "Magnetic Manipulation Instrumentation for Medical Physics Research," Rev. Sci. Instrum. 65, 533 (1994), and references cited therein. See also McNeil et al., "Functional Design Features and Initial Performance Characteristics of a Magnetic-Implant Guidance System for Stereotactic Neurosurgery," IEEE Trans. Biomed Engrg., 42, 793 (1995); Tillander, "Magnetic Guidance of a Catheter with Articulated Steel Tip," Acta Radiologa 35. 62 (1951); Frei et al, "The POD (Para-Operational Device) and its Applications," Med. Res. Eng. 5,11 (1966); U.S. Pat. No. 3,358,676 to Frei et al., issued Dec. 19, 1967, entitled "Magnetic Propulsion of Diagnostic or Therapeutic Elements Through the Body Ducts of Animal or Human Patients"; Hilal et al., "Magnetically Guided Devices for Vascular Exploration and Treatment," Radiology 113, 529 (1974); Yodh, et al., "A New Magnet System for Intravascular Navigation," Med. & Biol. Engrg., 6, 143 (1968); Montgomery et al., "Superconducting Magnet System for Intravascular Navigation," Jour. Appl. Phys. 40, 2129 (1969); U.S. Pat. No. 3,674,014 to Tillander, issued Jul. 4, 1972, entitled "Magnetically Guidable Catheter-Tip and Method"; and U.S. Pat. No. 3,794,041 to Frei et al., issued Feb. 26, 1974, entitled "Gastrointestinal Catheter." The full content of each of the cited documents are herein incorporated by reference in their entirety.

Unfortunately, the above-described technique requires the physician to react to the movement of the implanted device after the fact. There is no precise correlation of the imaging system with the medical magnetic manipulation, and no way to apply fields and/or force gradients precisely in needed directions. With hand-held magnets, the only feedback the surgeon could have was his observation of motion of a magnetic implant by x-ray or ultrasonic imaging in response to his movement of the magnet. The field producing magnet, so guided without direct visual display of the field lines, is controlled by the operator's estimate of the field direction and magnitude at a particular location of the implant. Since many combinations are possible, this essentially "blind operation" is bound to result in a somewhat random position and angulation as related to the needed field line direction and magnitude to provide guidance and/or pulling force. In difficult interference situations, it is difficult without such imaging guidance to provide even a reasonable guess as to a correct direction for the magnet axis to obtain field alignment with the intended path. The large electromagnet of Yodh et al. is one attempt to minimize the "blindness" of the approach just described, but the Yodh et al. approach still relies on operator judgment and vision, and is subject to such error. While multiple coil arrangements such as the magnetic stereotaxis system (MSS) described in McNeil et al. can be used to provide such guidance, it is difficult in such systems to provide a combined guiding force and force-applying field gradient in the same desired direction.

Clearly, both operation time and risk to a patient could be reduced if an apparatus and method were available to more accurately and rapidly guide or move a magnetic surgical implant. This device and method can either provide feedback to the physician guiding the implant so that the physician could predict the movement of the implanted device rather than react to it after the fact, or it can be used more automatically with computer-controlled motion along a physician-selected planned path. It would also be advantageous if simpler hardware and software could be used to locate the external magnet and provide more effective field solutions. The moveable magnet location should take into account an exclusion volume around the patient in which the magnet may not be located. In the case of neurosurgery, for example, the magnet cannot be located too closely to the patient's head, nor in the path of imaging X-rays.

SUMMARY OF THE INVENTION

It is thus an object of the invention to provide a rapid interactive display of the aligning torque and magnetic pulling directions of a magnet acting on a volume.

It is a further object of the invention to provide a physician with devices and methods that facilitate the prediction of the movement of a magnet implant in response to an externally applied magnetic field.

It is yet another object of the invention to provide devices and methods that facilitate rapid and appropriate adjustment of the position of an external magnet to steer a magnet internal to the body of a patient.

It is still another object of the invention to provide a moveable field-producing magnet that can be located and angled so as to provide flexibility in avoiding interference with imaging systems which may change between and during various surgical procedures.

It is another object of the invention to provide means whereby a physician can use voice control or other non-tactile control to govern path choice at arterial branches or lumenal branches so that both hands are available for other needs, in intravascular navigation applications.

It is yet a further object of the invention to provide an external magnet adapted to provide a magnetic field of sufficient strength and appropriate angular spread to provide flexibility in positioning and orienting the external magnet, even while respecting exclusion volumes around a patient's body.

These and other objects are achieved by the inventive methods and apparatuses to guide an implant disclosed herein. The invention provides rapid interactive display of the aligning torque and magnetic pulling directions of a permanent, a superconducting, or a resistive wire magnet acting on a volume, which volume may include a portion of a patient's body. The invention allows a hand-held, hand-positionable or servo-controlled external magnet to be moved external to the volume, while the resultant magnetic forces are displayed in real-time (essentially instantaneously, or at least as rapidly as is needed for effective surgical control) on a computer screen. In this way, a physician can rapidly adjust the position of an external magnet to steer a magnet internal to the body.

By placing a set of fixed fiducial marks on the magnet and using a device that can localize these marks in three dimensions, the position of the magnet can be associated with the treatment volume. The volume's position can be associated with the magnet by placing fiducial marks on the volume and "registering" these marks with the localizer, or by putting the volume in a standard place relative to the localizer. A second method of localizing the magnet includes putting magnetic sensors at appropriate fiducial points.

The magnetic field of any magnet can be simply measured and suitably mapped in three dimensions. At run time a pre-measured map can be superimposed on the imaging volume using the registration established by the fiducial marks.

Assuming that the volume has a set of images associated with it and fiducial marks that can be registered in the imaging volume, the magnetic field and force can be displayed and updated as the magnet is moved relative to the imaging volume. The field can be displayed at any point in the image set, and updated as the magnet is moved. Commercial ultrasonic and infrared localizers exist at present that give great accuracy (on the order of a millimeter) to this technique. One such localizer is described in U.S. Pat. No. 5,383,454, issued Jan. 24, 1995 to Richard D. Bucholz, which is hereby incorporated in its entirety by reference.

In one embodiment, an apparatus in accordance with the invention comprises a moveable magnet assembly having a plurality of fiducial marks thereon; a localizer comprising a plurality of imaging sensors configured to sense a position in three-dimensional space of the fiducial marks to thereby provide an indication of a location of the moveable magnet; and a processor including memory having stored therein a pre-measured representation of a magnetic field generated by the magnet assembly and a display configured to present a graphical representation of the magnetic field, the processor being configured to be responsive to the indication of the location of the moveable magnet provided by the localizer so that the display provides an indication of the magnetic field within a selected volume of space resulting from the magnet assembly when the magnet is at a position indicated by the localizer.

In accordance with another embodiment of the invention, a method for providing a rapid interactive display of the aligning torque and magnetic pulling directions of a magnet comprises the steps of providing a plurality of fiducial marks on the magnet assembly; sensing a location and orientation of the fiducial marks; computing a magnetic field in a selected volume of space produced by the magnet assembly when the magnetic assembly is in the sensed location and orientation; and displaying a representation of the magnetic field in the selected volume of space. This inventive method embodiment may further comprise the steps of placing a magnetic seed in a tissue of a living body; providing fiducial marks on an external surface of the living body proximate the tissue; sensing a location and orientation of the living body; and selecting the selected volume of space to include the tissue of the living body.

In another variation of the invention, the field lines need not be displayed. Instead, a vascular or other lumenal path displayed on the screen is surgeon identified as being the path of choice. The computer is then able to "know" in the treatment volume the direction needed for the guiding field at each point along the path. It can then provide orientation and positioning of the external, field-generating magnet as needed for navigation along the path. At arterial or other lumenal branch points, the surgeon can further assist the delicate navigational needs by voice commands understandable by the computer.

In other variations of the inventive methods and apparatuses, means are provided for locating and angling the external field producing magnet while avoiding interference with the imaging means, which may include an exclusion volume about a patient's body. In yet another variation, a permanent, superconducting, or resistive wire external field-generating magnet provides a "shaped" field, i.e., the near (and/or transition) field of the magnet is produced by a specially shaped coil and/or core to provide magnetic fields of sufficient strength and appropriate angular spread to provide additional flexibility in positioning the magnet during surgery. In the case of a superconducting magnet, the winding shape is adjusted. For a resistive wire magnet, the windings and core of the magnet may both be adjusted to accomplish the shaping.

These and other embodiments of the invention may be fully understood by those skilled in the art by reference to the drawings and to the detailed explanation that follows.

DESCRIPTION OF THE PREFERRED EMBODIMENTS

As used herein in this description and in the claims that follow, unless otherwise explicitly qualified or made clear by the context in which it appears, the term "magnet," when referring to a magnet external to a patient, is intended to include both single magnets (of either the permanent or electromagnetic variety) and assemblies of a plurality of magnets in which the individual magnets of the assembly are used in conjunction with one another to produce an effective magnetic field.

Figure 1:
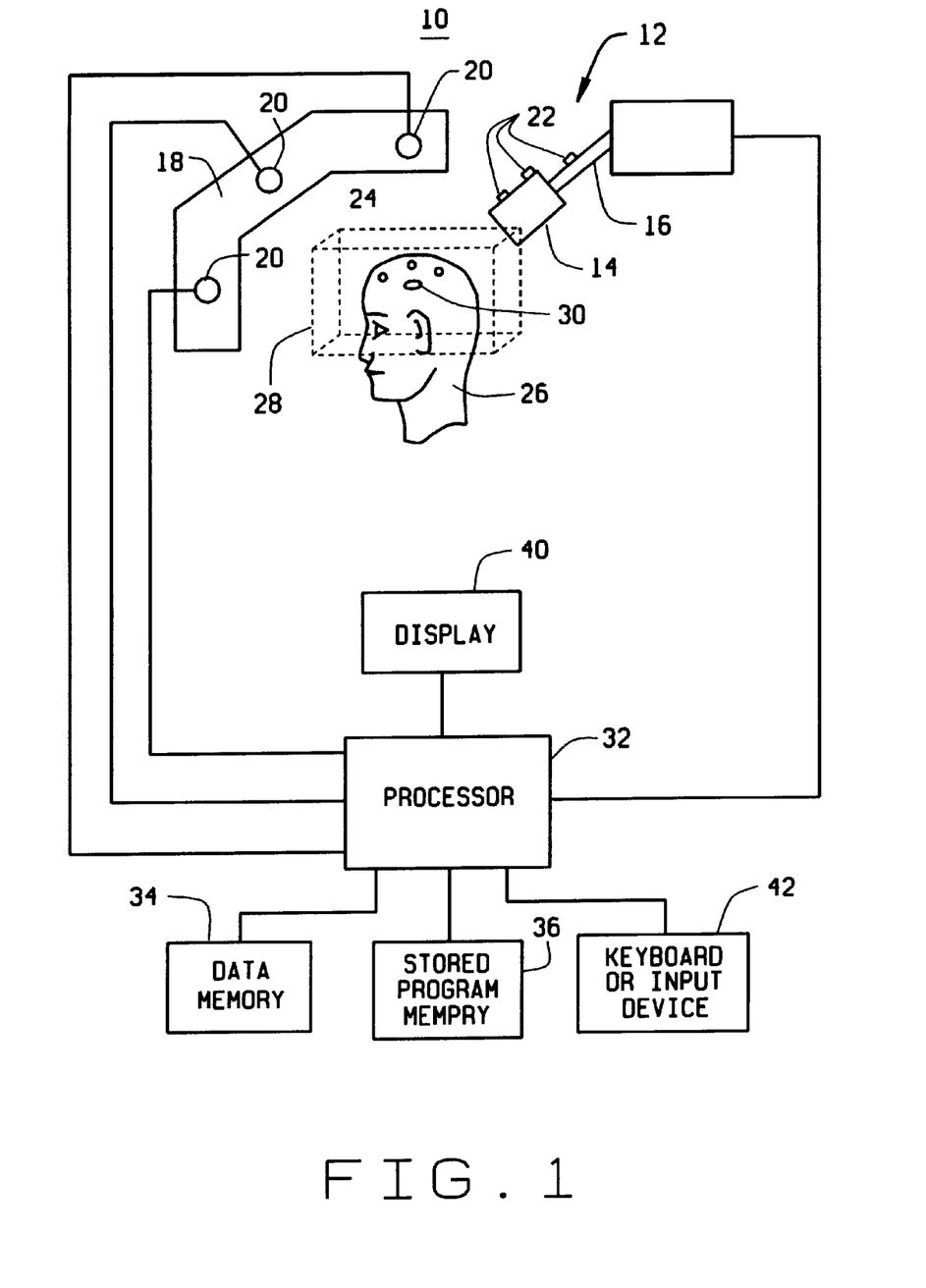
FIG. 1 is a block diagram representation illustrating an embodiment of a device in accordance with the invention.

FIG. 1 is a schematic representation of an embodiment of a device 10 in accordance with the invention. A moveable magnet assembly 12 including a magnet 14 is provided. Magnet assembly 12 may be a gantry supporting the weight of magnet 14. Magnet 14 may be either a strong permanent magnet, a superconducting electromagnet, or a resistive wire electromagnet, although a strong permanent magnet may require additional articulation to compensate for its lack of current control and magnitude. Motion of the magnet assembly 12 may be automatically controlled, such as with a computer- or servo-controlled robotic arm 16 or other equivalent mechanical manipulation device to provide the needed orientation, location, and consequent coil current required to align its magnetic field with the desired motion of a magnetic object 30 to be guided. However, automatic control is not required by the invention. Thus, magnet assembly 12 may simply comprise a permanent magnet 14 at the end of a wand 16 (rather than a robotic arm) that a surgeon manipulates by hand. If automatic control or gantry support is provided, however, the apparatus can smoothly manage relatively large electromagnetic coils 14, and can therefore apply strong magnetic fields, so as to provide guidance or force deeper into the body 26.

Device 10 further comprises a plurality of localizers 20, which may be mounted on a localizer assembly 18. The plurality of localizers 20 each comprise a camera-like sensor (such as a commercial infrared, optical, or ultrasonic sensor) that senses fiducial marks 22 on magnet assembly 12. A general discussion of localizer technology of a type that may be employed in the present invention will be found in previously-mentioned U.S. Pat. No. 5,383,454. Fiducial marks 22 on magnet assembly 12 may be any marker that can be located by the plurality of localizers 20, and may preferably comprise lighted LEDs (light emitting diodes). Optionally, additional fiducial marks 24 may be applied to a patient's body 26 or part thereof (in the illustrated case, a patient's head). Fiducial marks 24 may either be screw-in or stick-on markers. Screw-in markers are preferable for the greater accuracy that may be obtained. Alternately, anatomical landmarks can be used, especially if the location of the volume of interest 28 is known relative to localizers 20 and a CAT, X-ray or MRI medical imaging device is used in conjunction with the localizers 20 (as is normally contemplated). However, the use of anatomical landmarks may result in less accurate display of the magnetic field of magnet 14 relative to the patient's body 26 and any magnetic seed 30 or other surgical device embedded in the patient's body. (The term "seed" is intended to encompass all types of magnetic probe masses or other magnetically guided or pulled implanted surgical, diagnostic, or therapeutic objects in the body.)

While mounting of localizers 20 on a localizer assembly 18 is desirable, any alternate means of positioning and directing the localizers at a specified volume of space in which fiducial marks 22 may be located when magnet assembly 12 is in use may be used. It is only necessary that fiducial marks 22 be positioned in such a way that the position and orientation of the magnet 14 in three-dimensional space can be sensed by localizer 20 relative to a specified volume of interest 28. In practice, this volume of interest 28 would include the location within which the portion of the patient's body 26 in which a seed 30 or magnetic guidance tip (such as at the end of a catheter) is embedded when an operation is performed, and is preferably within a magnetic resonance imaging (MRI) or other area sensed by such means as would normally be employed during magnetic surgery. Seed 30 or magnetic guidance tip may comprise a permanent magnet, or an induced magnet of a permeable material. For simplicity, either type of material may be referred to as a "magnet" for purposes of describing the implant. Fiducial marks 24 must either be located by tracking them with a lighted probe (such as a probe with LEDs) or by touching a calibrated portion of the magnet to each in turn. A sufficient number of localizers 20 and fiducial marks 22 are provided to enable a processor 32 receiving signals from localizers 20 to accurately determine the position and orientation of magnet 14. If fiducial marks 24 are provided on the patient's body 26 for the purpose of locating the position and orientation of the patient's body 26 relative to magnet 14, a sufficient number of these such marks 24 are also provided to enable the processor 32 to make a determination of the location and orientation of the patient's body 26. Any fiducial marks 24 provided on patient's body 26 would be of a type that would also appear in a CAT, X-ray, or MRI scan in order for these images to be registered.

Localizers 20, whether optical, infrared, ultrasonic, magnetic, or otherwise, detect the position of the markers 22 on magnet assembly 12 and provide a signal or signals to processor 32. It will be understood that the nature of the communications link between localizers 20 and processor 32 is not critical, nor is it critical as to whether a separate link is provided between each localizer 20 and processor 32 or whether data from all the localizers 20 is combined and sent through a single link. Processor 32 is also provided with memory 34 in which is provided data representative of the magnetic field in three dimensions produced by magnet 14, and memory 36 in which is provided a stored program containing instructions for processor 32. (Memory 34 and memory 36 in FIG. 1 may be any suitable, conventional form of memory and may comprise different addresses or locations in the same physical memory element.) The representation for the magnetic field may be a set of measured data or a set of parameters for magnet 14 from which the magnetic field can be calculated. If magnet 14 can be one of several magnets of varying strength or size, data or parameters for several representations of magnetic field, each representing a different magnet, may be stored in memory 34. If magnet 14 is an electromagnet rather than a permanent magnet, the data or parameters in memory 34 may be scaled in accordance with an amount of current flowing through magnet 14. Data representing this amount of current would be made available as an input (not shown) to processor 32, preferably as a signal obtained from a power supply of magnet 14 or an ammeter (neither of which is shown).

In some modes of operation, the processor 32 will, in addition to the above tasks, calculate the current needed by the electromagnet 14 to optimally provide a field at the location of seed 30. The position, orientation, and current of magnet 14 will be optimized simultaneously by processor 32 so as to yield the needed navigation with a minimum of magnet motion. In such modes, the processor will send a signal (not shown) to the electromagnet power supply.

The program provided in memory 36 instructs processor 32 to calculate, from the localizer inputs that result from fiducial marks 22, the location and orientation of magnet 14 relative to the volume of interest 28. From this location and orientation, the program further instructs processor 32 to provide a display representative of the resulting magnetic field within the volume of interest 28. In "manual mode," i.e., the mode in which a surgeon navigates visually rather than by directing overall computer navigation choices, this display would be shown on the surgeon's display 40.

Otherwise, a second engineering display (not shown) would present these features. Preferably, the location of fiducial marks 24 on the patient's body 26 are also displayed. The representative display of the magnetic field is preferably graphical, and is presented in a fashion that is useful to a surgeon during an operation. For example, a two-dimensional view in a plane including seed 30, or a rotatable three-dimensional perspective view may be provided. A selection of one or more different types of views may be provided, based upon operator input, such as through a keyboard, a mouse, a joystick, or other input device or devices 42 communicating with processor 32. The input device or devices 42 may also be used in a manner described below to initialize the necessary coordinate system transformations to be performed by processor 32.

Data received from localizers 20, and the processing by processor 32 to present a graphical representation on display 40 of the magnetic field produced by magnet 14 must be fast enough to provide "real-time" feedback for a surgeon; i.e., the feedback must be rapid enough to allow decisions to be made during a surgical procedure involving the movement of the implanted magnetic device 30. The method of Procrustes is used to compute the 4×4 rigid body transformation between coordinates in the imaging system and coordinates in the localizer system. Thereafter, the 4×4 matrix may be applied to transform a pre-stored representation of a magnetic field into a magnetic field having the position and orientation sensed by localizers 20 using standard programming techniques on a presently-available Intel PENTIUM®-based processor (such as a typical PC), or a Silicon Graphics workstation, with the transformation being accomplished in sufficient time to provide a display that is updated rapidly enough for surgical purposes.

Preferably, at least three, or even more preferably, four fiducial marks 22 are provided on magnet assembly 12, and the same number of fiducial marks 24 on the patient's body 26. Also preferably, display 40 may also provide a display of a simultaneously obtained CAT, X-ray, or MRI image. The CAT, X-ray, or MRI image can be superimposed upon the display of the magnetic field. If the fiducial markers 24 on the patient's body 26 are of a type that shows up on the CAT, X-ray, or MRI image (e.g., metal screw-in markers), then the magnetic field display and the CAT, X-ray, or MRI image may be aligned or registered either automatically by processor 32 or manually by the surgeon. Alternatively, or in addition to the CAT, X-ray, or MRI imaging device, a magnetic locating device such as that described in U.S. Pat. No. 5,558,091, issued Sep. 24, 1996 to Acker et al. (which is hereby incorporated by reference in its entirety) may be used for determining and displaying a position and orientation of implanted seed 30. It is also possible to use the magnet being used to guide the implant as the source of the magnetic field for determining the location of the implant, in accordance with the devices and methods disclosed in "Method and Device for Locating Magnetic Implant by Source Field," a U.S. Patent Application to R. Ritter et al. filed on even date herewith and hereby incorporated in its entirety by reference.

A typical use of the inventive apparatus would proceed as follows: First, a patient's head (or other body part to undergo a magnetically-aided surgical procedure) would be supported in a fixed position in space relative to localizers 20, with fiducial marks 24 (or anatomical landmarks) on patient 26 visible to localizers 20. A representation of the field of view of localizers 20 then appears on display 40. Fiducial marks 24 (or anatomical landmarks) are then identified on display 40 by touching the actual physical locations on patient 26 with magnet 14 or in some other suitable fashion. The image coordinates are related to localizer coordinates using the method of Procrustes. Next, the location of magnet 14 is determined by localization of fiducial markers 22. Once the location of the magnet 14 is known, processor 32 then relates the coordinate system of the stored representation of the magnetic field in memory 34 to the coordinate system of the images using simple matrix multiplications. A representation of the magnetic field of magnet 14 in the coordinate system of display 40 is then presented on display 40, preferably together with a representation of the part of the body of patient 26, fiducial markers 22 and 24, and magnetic seed or guidance magnet 30. As the magnet 14 is moved, positions of the fiducial markers 22 change and are detected by localizers 20, and the resulting magnet 14 positions determined. In manual mode, display 40 is continuously updated to show the resulting magnetic field in the coordinate system of display 40. In automatic mode, the equivalent information is updated within processor 32. Preferably, a current location of seed or guidance magnet 30 is also shown on display 40.

Figure 2:
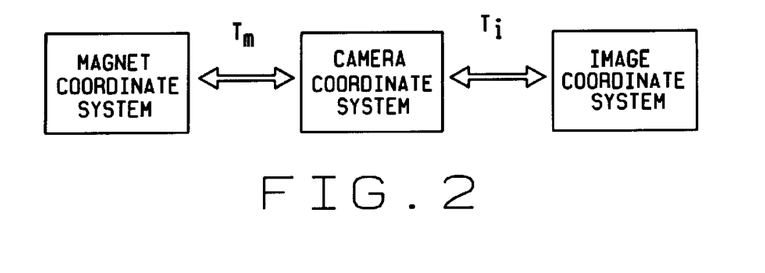
FIG. 2 is a block diagram showing how coordinate systems relative to a magnet, a set of localizers (cameras), and an image on a display are related.

FIG. 2 shows, in block diagram form, the relationship between various coordinate systems of interest in the inventive system. The magnet coordinate system refers to a coordinate system referenced to magnet 14. The representation of the magnetic field of magnet 14 that is stored in memory 34 is likely to be most conveniently represented relative to this coordinate system. The camera coordinate system refers to the coordinate system of localizers 20, and may be fixed depending upon the construction and positioning of localizer assembly 18. The image coordinate system refers to the three-dimensional coordinate system of the image of the patient on display 40. Because the positions of the LEDs (or other fiducial markers 22) on magnet assembly 12 are known in advance relative to the magnet coordinate system, once the actual positions of the LEDs are known, the magnetic field can be converted easily to the other coordinate systems using transformations $T_m$, $T_i$, or a combination of both transformations (which may be applied in a single step, rather than two separate transformations). These transformations are normally carried out by multiplications involving 4×4 transformation matrices. Typically, the LEDs that may be used as fiducial markers 22 may be infrared LEDs that are detected by cameras sensitive to infrared radiation and used as localizers 20. Processor 32 receives information from localizers 20 from which it can compute the position of the LEDs (or the localizer array may contain its own processor to do this and supply processor 32 with this information directly). When the patient's body is fixed in position and fiducial markers 24 touched by a point known relative to the magnet, the positions of fiducial markers 24 relative to the LEDs (i.e., fiducial markers 22, the positions of which are known in advance) are determined. The identification of the corresponding marks on display 40 identifies the corresponding positions in the image coordinate system. $T_i$ is then computed using the method of Procrustes. Finally, as the magnet 14 is moved, the positions of the LEDs are changed and detected by the array of localizers 20, and the transformation $T_m$ is determined and continuously updated. Concatenations of transformations of $T_m$ and $T_i$ are continuously performed to update display 40 or the processor control memory.

Figure 3:
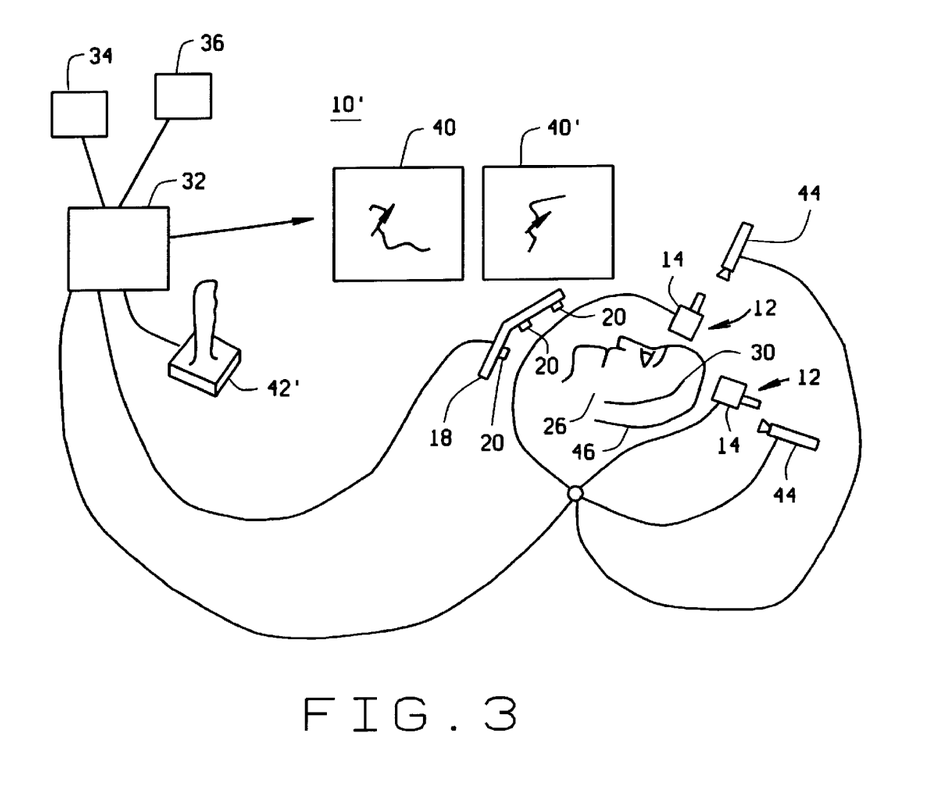
FIG. 3 is a block diagram illustrating another embodiment of a device in accordance with the invention.

FIG. 3 is a block diagram of another embodiment of the inventive apparatus 10'. In this embodiment, a joystick 42' is used as an operator input to processor 32, possibly in conjunction with other standard input devices such as a keyboard (not separately shown). More than one magnet assembly 12 may be provided, each with a separate magnet or magnets 14, in which case memory 34 may be provided with a plurality of magnetic field representations, each representing a particular magnet or magnets 14 on a magnet assembly 12, or it may be provided with only one magnetic field representation, if the magnetic fields of magnets 14 are sufficiently similar. Magnet assemblies 12 in this case are moved in this embodiment under control of operator input device 42' or another suitable input device or devices, and if magnets 14 are electromagnets, the current through magnets 14 may also be controlled via operator inputs. Localizers 20 and processor 32 are configured to locate each of the magnets 14, and processor 32 is configured to compute the magnetic fields from each of the magnets 14, compute a resultant total magnetic field, and display the representation of the resultant total magnetic field on displays 40 and 40'. (In this embodiment two displays [40 and 40'] are provided as an aid to the surgeon. It will be understood that as many displays as are deemed necessary may be provided.) Possibly different colored LEDs may be provided on the individual magnet assemblies 12 so that their separate locations are more readily determined. Preferably, if a plurality of magnet assemblies 12 are provided, they may be used either independently or in unison, as required.

Processor 32 also controls two X-ray tubes 44 (one for each display 40, 40'). For each X-ray tube 44, there is one sensor (camera), not shown, the output of which is the signal sent to processor 32 to provide the displays. These X-rays provide real-time imaging of patient 26 as well as a surgical device 46 being steered by the magnetic fields of magnets 14. Preferably, the fluoroscopic imaging system is immune to magnetic fields, because of the presence of the strong fields from nearby magnet 14. Sensors for fluoroscopic imaging systems meeting this requirement include charge coupled devices (CCDs), micro channel plates (MCPs), and amorphous silicon technologies. In this case, surgical device 46 is a catheter having a magnetic tip 30. Images provided by X-ray from tubes 44 are superimposed on the magnetic field image on displays 40 and 40' to indicate the progress of the surgical procedure to allow a surgeon to determine how to position magnet assemblies 12 (and possibly control currents in magnets 14) as the operation proceeds. The images provided by X-ray tubes 44 may be provided by sensors (not shown) that provide image inputs to processor 32. It will be recognized that many components, such as magnets 14, X-ray tubes 44, displays 40 and 40', input devices 42', etc., may be provided in such numbers as needed, if processor 32 (which itself may comprise a plurality of processors) is provided with the appropriate stored program.

In each of the embodiments of the invention, magnet or magnets 14 are orientable and positionable about a patient's body 26. The best orientation is commensurate with the display, and with avoiding imaging equipment (including X-ray tubes 44 and corresponding sensors) and parts of body 26 itself, which in prior art methods would interfere with adequate positioning and orientation of a magnet. Often, in common usage, a magnet which pulls or aligns an object does so along its axis, but the inventive apparatuses and methods disclosed herein do not require this limitation. These apparatuses and methods provide optimization of the magnetic field strength and minimization of current needed for energization of external magnet 14 (or the plurality of external magnets 14, if more than one is provided).

Several versions of the control of the manipulation can be employed. In a form employing the least amount of automatic control, screens 40 and 40' display magnetic field lines, either in two (preferably orthogonal) projections, or in a three dimensional representation that can be rotated or otherwise manipulated on a screen. A surgeon-operator manipulates magnet 14 (such as by moving magnet assembly 12), which in turn moves the magnetic field line display on the display screen or screens (such as screens 40 and 40'), so that the field direction at the location of the implant is made to agree with a desired and displayed direction of motion of the implant. The ability to accomplish this directional agreement, even in the presence of restraints set by potentially interfering imaging components and parts of the body, is greatly facilitated by the shape of the magnetic field lines.

In moving away from the axis of an electromagnetic coil used for magnet 14, magnetic field lines increasingly curve away from the straight line of the on-axis field of the coil. These magnetic field lines have azimuthal symmetry about the coil axis, which often adds to the freedom of coil orientation. Thus, locating and orienting the field source magnet 14 so that a curved field line falls on the location of the magnet, makes possible a direction control that would otherwise be geometrically impossible, because of spatial constraints in many cases, if the axis of magnet 14 had to align with the motion direction of seed 30.

If attainment of a specific field strength is required by the control program, the use of current control (and/or closeness of magnet 14) provides an accommodation to the use of the curved field line. In a typical coil, the field strength of the magnetic field at a given distance from the coil is reduced as an implant 30 is moved off axis and to a location of more curved field lines. For a purely manual version of control, the position of and/or current in the magnet 14 may be adjusted by the operator in response to marked regions of the displayed lines, which may be marked in distinctive colors. Distinctive colors or other suitable markings may be displayed to indicate avoidance regions, i.e., regions so close to a seed 30 or other implant that an undesired magnitude of field or gradient is present at the seed or implant. By avoiding positioning of magnets 14 in the avoidance region or regions, means other than the imposition of a magnetic force or torque on the implant (such as mechanical motion of a catheter to which the magnetic seed 30 is attached at an end) may be used for moving it, if desired. Segmentally colored lines on display 40 and/or 40' may also be used to help guide an operator in his manual manipulation of a magnet or coil by facilitating the choice of more advantageous position and angle combinations for magnet 14 for applying a specified magnetic field magnitude and direction at the location of seed or implant 30.

In use, the inventive apparatus causes the magnetic seed or implant 30 to align with the magnetic field direction at its location in the body 26. In addition, if a pulling force is required, the direction of the gradient on the aligned implant is also along the field line (in an antiparallel direction). If seed 30 is a magnetically permeable implant or an appropriately oriented permanent magnet implant, the implant 30 is naturally guided along the field line and pulled along it, if desired.

By "shaping" of a magnetic field, it is meant that magnetic field lines of either the near field or the transition field of the magnet, or both, are given a known or readily determinable shape useful for manipulating magnetic seed 30, particularly in positions where it would be difficult to apply an on-axis field of proper orientation and magnitude due to an exclusion region, or where it is desirable to guide or pull the magnetic seed 30 along a curved path corresponding to a field line of the shaped magnetic field. The "near field" of a magnet is defined as the field of the magnet that is close enough to the source (which may be an electromagnetic winding) such that it does not correspond to a sufficiently close approximation of the standard dipole field shape for surgical guidance purposes. The near field of a finite source differs from a point dipole field significantly, for present purposes, when the field point is within 3 to 4 times the largest dimensions of the finite source, such as the greater of the width or length of a coil. A "transition field" is also defined between the near field and the dipole field, if the magnet is a single coil, or between the near field and the higher multipole field, in the case of a multicoil system. It is contemplated that computer or processor 32 (see, e.g., FIG. 1) will preferably have sufficient data and instructions in software to compute the near and transition fields of a magnet 14 for use for automatic control of magnet 14 or for display on display units 40, 40' in the case of manual control. Of course, guidance and pulling of a seed 30 may also be accomplished using the far field of magnet 14, but with the additional information that is preferably available to processor 32, the off-axis components of the magnetic field of magnet 14 may also become useful for guidance and pulling of seed 30.

Figures 4A, 4B, 4C:
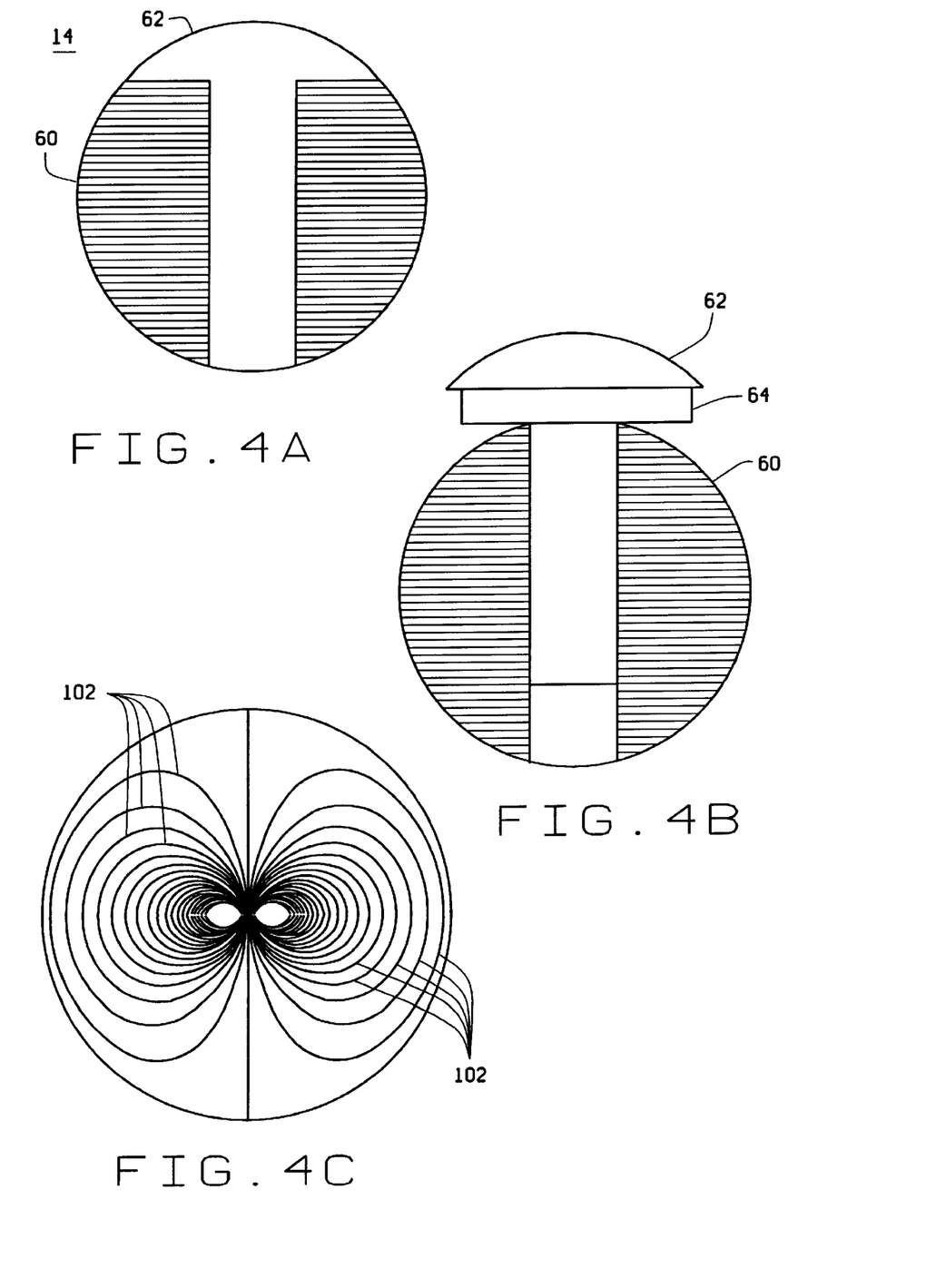
FIG. 4A is a side plan view of an embodiment of an electromagnet having a shaped magnetic field in accordance with the invention.
FIG. 4B is a side plan view of the electromagnet of FIG. 4A showing how "magnetic lensing" is accomplished.
FIG. 4C is an illustration of a representative field of a single coil magnet showing off-axis field lines.

One embodiment of a magnet 14 configured to provide a "shaped" magnetic field suitable for use with the inventive apparatus is shown in FIG. 4A. Winding 60, which may be a resistive wire winding, is wound in the shape of a sphere. With automated winding equipment, a spherical winding may be readily made by winding more layers in a central portion of the sphere to produce a bulge in the middle section of winding 60. For a superconductive winding, the special form of winding 60 alone, without a core, is adequate to provide a sufficiently "shaped" magnetic field. For a resistive winding, a core 62 of permeable magnetic material is provided to shape the magnetic field in conjunction with the special form of winding 60. The embodiment illustrated here has a mushroom-like shape. Of course, other embodiments are possible, including those in which magnet 14 is a permanent magnet of predetermined shape.

A permanent or resistive wire magnet 14 can be made to provide "magnetic lensing." A segment of permeable material, such as core 62, may be inserted in winding 60 (or in a hollow permanent magnet) and moved longitudinally along the front of the permanent magnet or inside the winding of the resistive wire magnet to change the shape of the field lines to accomplish a particular procedure. Different segments of permeable material may also be substituted to provide different amounts of shaping of the magnetic field. Spacer rings 64 may be provided, as shown in FIG. 4B, to prevent "suck-in" of the core material 62 that would otherwise occur with a permanent magnet 60, or when a winding 60 is energized.

Control of the magnetic field strength applied to seed 30 is easily accomplished. In a manual embodiment, the operator manipulates the external magnet 14 in response to the magnetic field lines displayed on the display system 40, 40' so that the magnetic field lines and magnitude of the magnetic field are configured to provide the correct magnitude and direction at the location of seed 30 to provide the desired motion or guidance of seed 30. Control of the magnetic field may also be done by software running in control computer 32. In this case, the screen display 40, 40' provides confirmation of the operation of the system to the operator.

In yet another embodiment of the inventive apparatus, display system 40, 40' is less important, and it is not used in the same manner. Instead, the computer 32 is provided with an optimization program in software that processes the input information of the implant position and direction of the desired motion, and processes this information with predetermined motion algorithms to effect a desired motion. In this mode, the forbidden regions (i.e., the regions including the body and the imaging system that must be avoided by magnet system 12) are provided as data to computer 32 or are determined by computer 32 in some suitable manner. The computer 32 then, through software control, provides the desired alignment in a manner similar to that described above. Off-axis field lines of magnet 14 (such as lines 102 of a single coil magnet as shown in FIG. 4C) may be used to greatly increase the effective directions of the magnet, and in fact provide complete coverage of the procedure region in patient 26 despite the forbidden exclusion regions.

Figure 5A:
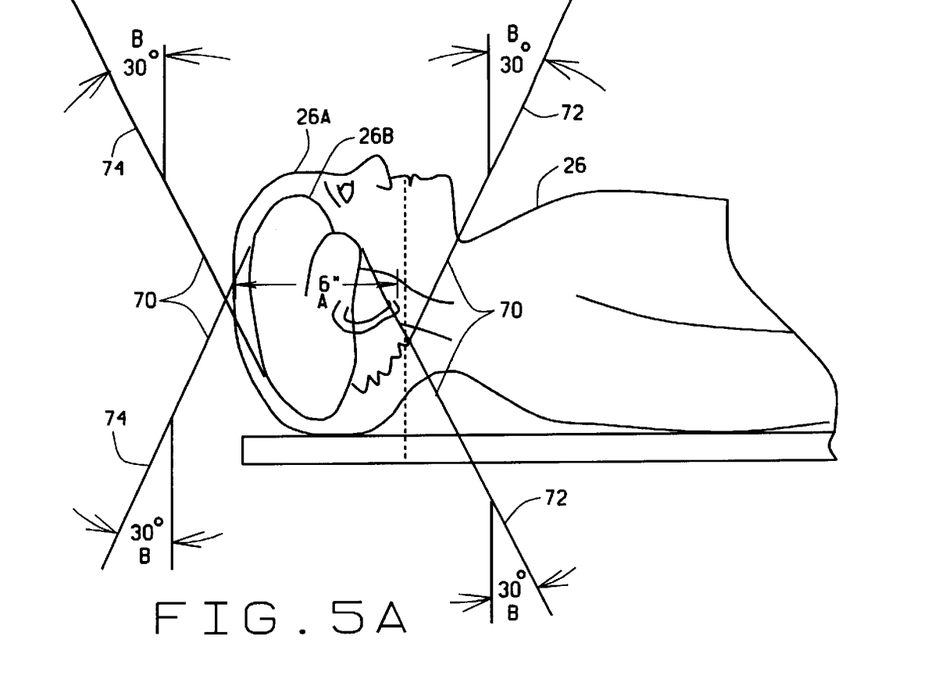
FIG. 5A is an illustration of a typical exclusion zone for neurosurgery.
Figure 5B:
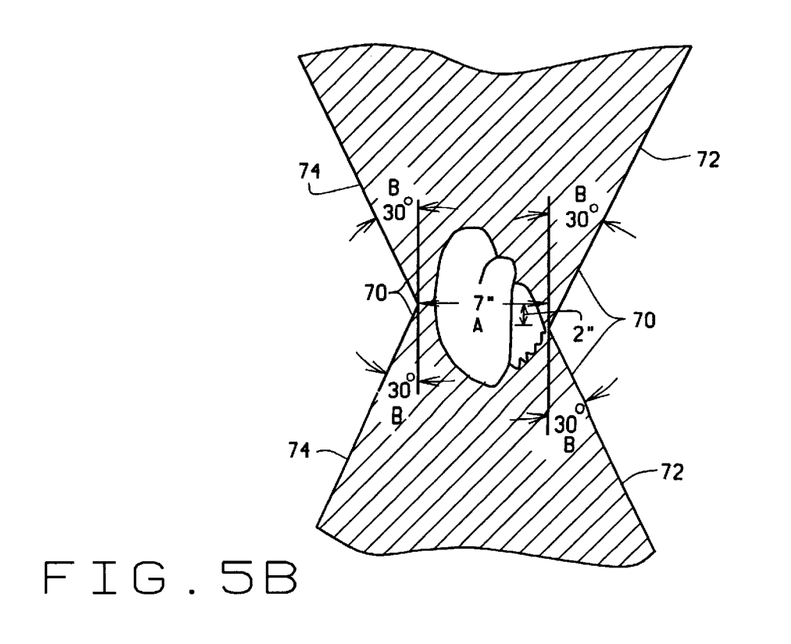
FIG. 5B is another illustration of the exclusion zone of FIG. 5A showing both a typical cumulative mechanical zone of exclusion and a typical maximal operating volume for a magnetic catheter in a brain.

FIG. 5A is an illustration of a typical exclusion region in a neurosurgical procedure. The exclusion region 70, in which X-ray beams pass, is defined by two cones 72 and 74. The tips of the two cones 72, 74 are separated by about 6". The conical regions are slightly offset from one another, so that near the patient's neck, the intersection is about 2 inches lower than at the top of the head. This detail is better shown in FIG. 5B, and is represented as dimension C. (For present purposes, it may be assumed that other exclusion regions exist, including one that encompasses the entire body 26. However, magnet 14 and magnetic assembly 12, neither of which is shown in FIGS. 5A or 5B, may be provided with mechanical limitations that would prevent their positioning that far away from the patient's head 26A. Therefore, it is not necessary to provide a control computer with data detailing the shape of exclusion regions beyond the limits of motion of magnet 12 and magnetic assembly 14.) In FIGS. 5A and 5B, dimension A is typically about 6 or 7 inches, and angles B are typically about 30°. The illustrated exclusion zone 70 comprising cones 72, 74 provides ample room for manipulation of a magnet 14 having a shaped field on the left, right, and top of the head 26A, and perhaps some other areas, without interfering with an imaging apparatus, parts of which are typically located above and below the patient's head. The exclusion zone 70 shown here represents the typical cumulative mechanical zone of exclusion and imaging beam zone of exclusion to accommodate 2" X-ray equipment. FIG. 5B better shows the typical maximal operating volume 26B of a magnetic catheter (not shown) with respect to exclusion zone 70.

The inventive apparatus may be used to perform magnetic surgery by a method comprising the steps of implanting a magnetic seed in the body of a patient, producing a medical image (such as an X-ray image) of the region of the patient's body including the implanted seed, superimposing a representation of the magnetic field lines of an external magnet (i.e., magnet 14) on the medical image, aligning a portion of the superimposed representation, such as a near-field magnetic field line of the external magnet, along an intended path of the seed, and moving the external magnet into a position to produce the represented superimposed magnetic field to effect guidance or movement of the seed. If the magnet is a permanent magnet, the alignment and movement steps would occur simultaneously. If the external magnet is an electromagnet, either normally conducting or superconducting, the alignment step may occur first, followed by servo-controlled movement of the magnet.

The inventive apparatus may also be used in a method comprising the steps of implanting a magnetic seed in a patient's body; imaging a region of the patient's body including the implanted seed to thereby produce a medical image; storing information indicative of a path to be taken by the seed in a memory of a computer having a display; displaying a representation of the path and a current location of the seed on the display; calculating orientations and currents of an external electromagnet required to provide a magnetic field to the seed to move the seed along the path; activating a servo-controlled motor to move the external electromagnet to the calculated orientations; providing the calculated currents to the electromagnet; and updating the display to provide current locations of the seed relative to the path. Commands may be provided to the computer by non-tactile means, such as by an operator speaking into a voice recognition unit that provides input to the computer.

One skilled in the art would recognize that numerous modifications are possible to the specific embodiments described herein while remaining within the spirit of the invention. Therefore, the scope of the invention should be determined with reference to the claims below and the entire range of equivalents permitted under applicable law.

What is claimed is:

1. An apparatus for providing rapid interactive display of the aligning torque of a magnet, the apparatus comprising:
   (a) a moveable magnet assembly having a plurality of fiducial marks thereon;
   (b) a localizer comprising a plurality of imaging sensors configured to sense a position in three-dimensional space of the fiducial marks to thereby provide an indication of a location of the moveable magnet assembly; and
   (c) a processor including memory having stored therein a representation of a magnetic field generated by the movable magnet assembly and a display configured to present a graphical representation of the magnetic field, the processor being configured to be responsive to the indication of the location of the moveable magnet assembly provided by the localizer so that the display provides an indication of the magnetic field within a selected volume of space resulting from the movable magnet assembly when the magnet is at a position indicated by the localizer.

2. The apparatus of claim 1 and further comprising a medical imaging device, and wherein an image sensed by the medical imaging device is superimposed upon the indication of the magnetic field within the selected volume of space.

3. The apparatus of claim 2 wherein the moveable magnet assembly is coupled to the processor and further comprising an operator input device coupled to the processor and operable to control a location and orientation of the movable magnet assembly.

4. The apparatus of claim 3 in which the operator input device is configured for non-tactile operator input.

5. The apparatus of claim 4 in which the non-tactile operator input device comprises a voice-recognition device.

6. The apparatus of claim 5 wherein the moveable magnet assembly comprises an electromagnet.

7. The apparatus of claim 6 wherein at least some of the fiducial marks on the moveable magnet assembly comprise light emitting diodes (LEDs).

8. The apparatus of claim 1 and further comprising a plurality of fiducial markers configured for positioning on a portion of a patient's body.

9. A method for providing a rapid interactive display of the aligning torque of a magnet assembly, the method comprising:
   (a) providing a plurality of fiducial marks on the magnet assembly;
   (b) sensing a location and orientation of the fiducial marks;
   (c) computing a magnetic field in a selected volume of space produced by the magnet assembly when the magnet assembly is in the location and orientation of the fiducial marks; and
   (d) displaying a representation of the magnetic field in the selected volume of space.

10. The method of claim 9 and further comprising:
    (a) placing a magnetic seed in a tissue of a living body;
    (b) providing fiducial marks on an external surface of the living body proximate the tissue;
    (c) sensing a location and orientation of the living body; and
    (d) selecting the selected volume of space to include the tissue of the living body.

11. A method for providing a rapid interactive display of the aligning torque of a magnet assembly, the method comprising:
    (a) positioning a body part of a patient in a fixed position in space relative to a plurality of localizers;
    (b) displaying a view of the body part within a field of view of the localizers on a display;
    (c) identifying landmarks on the body part;
    (d) locating fiducial marks on a moveable magnet assembly;
    (e) computing a position and orientation of the movable magnet assembly;
    (f) determining relationships between a coordinate system of the display, the magnetic assembly, and a stored representation of a magnetic field produced by the movable magnet assembly;
    (g) converting the representation of the magnetic field into display coordinates; and
    (h) displaying a representation of the magnetic field in display coordinates on the display.

12. The method of claim 11 wherein the identification step comprises the touching of markers selected from the group consisting of anatomical landmarks and fiducial markers with a localizing device.

13. A device for navigating a surgical, diagnostic, or therapeutic object in a patient's body, the device comprising:
    a) an external magnet mounted on a gantry having an adjustable attitude;
    b) a magnetic seed configured for implanting in a patient's body; and
    c) an imaging system configured to display a medical image of the magnetic seed implanted in a patient's body and to superimpose thereon a representation of magnetic field lines of the external magnet, including those representing a near field, the superimposition being dependent upon an orientation and location of the external magnet.

14. The device of claim 13 and further comprising a servo-system mechanically coupled to the gantry.

15. The device of claim 14 wherein the servo-system is configured to provide exclusion zones into which movement of the external magnet and gantry are prevented.

16. The device of claim 13 wherein the imaging system is configured to display two orthogonal projections of the medical image.

17. The device of claim 13 wherein the imaging system is configured to display a rotatable three-dimensional representation of the medical image.

18. The device of claim 13 wherein the imaging system comprises a magnetic field-immune, fluoroscopic imaging system.

19. The device of claim 18 wherein the imaging system comprises a sensor selected from a group consisting of charge coupled device sensors, micro channel plate sensors, and amorphous silicon sensors.

20. A method of magnetic surgery using an external magnet comprising the steps of:
(a) implanting a magnetic seed in a patient's body;
(b) imaging a region of the patient's body including the implanted seed to thereby produce a medical image;
(c) superimposing on the medical image a representation of a set of magnetic field lines of the external magnet, including those representing a near field, the superimposition being dependent upon an orientation and location of the external magnet;
(d) aligning a portion of the superimposed representation along an intended path of the magnetic seed; and
(e) moving the external magnet into a position outside of the patient's body to produce the magnetic field represented by the aligned superimposed representation to effect guidance or movement of the seed.

21. The method of claim 20 wherein the external magnet is a permanent magnet, and the aligning and moving steps occur simultaneously.

22. The method of claim 20 wherein the external magnet is an electromagnet, the alignment step occurs first, and the movement step is servo-controlled.

23. A method of computer-aided magnetic surgery comprising the steps of:
(a) implanting a magnetic seed in a patient's body;
(b) imaging a region of the patient's body including the implanted seed to thereby produce a medical image;
(c) storing information indicative of a path to be taken by the seed in a memory of a computer having a display;
(d) displaying a representation of the path and a current location of the seed on the display;
(e) calculating orientations and currents of an external electromagnet required to provide a magnetic field to the seed to move the seed along the path;
(f) activating a servo-controlled motor to move the external electromagnet to the calculated orientations;
(g) providing the calculated currents to the electromagnet; and
(h) updating the display to provide current locations of the seed relative to the path.

24. The method of claim 23 further comprising providing a non-tactile command to the computer.

25. The method of claim 24 wherein the step of providing a non-tactile command to the computer comprises speaking the command to a voice-recognition unit.

26. A device for navigating a surgical, diagnostic, or therapeutic object in a patient's body, the device comprising:
a) an external magnet mounted on a gantry having an adjustable attitude;
b) a magnetic seed configured for implanting in a patient's body; and
c) a magnetic locating device for determining and displaying a position and orientation of an implanted magnetic seed.

* * * * *